United States Patent [19]

Colella et al.

[11] 4,048,229
[45] Sept. 13, 1977

[54] α-AMINOMETHYL-4-HYDROXY-3-METHYLSULFONYL BENZYL ALCOHOLS

[75] Inventors: Donald F. Colella, West Norriton, Pa.; Carl Kaiser, Haddon Heights, N.J.

[73] Assignee: SmithKline Corporation, Philadelphia, Pa.

[21] Appl. No.: 539,492

[22] Filed: Jan. 8, 1975

[51] Int. Cl.$^2$ .............................................. C07C 91/18
[52] U.S. Cl. ........................ 260/570.6; 260/340.5 R; 260/343.7; 260/501.11; 260/501.12; 260/501.17; 260/501.18; 260/501.19; 424/280; 424/282; 424/316; 424/330; 260/570.5 C; 260/592
[58] Field of Search ........... 260/570.6, 501.19, 501.18, 260/501.12, 501.11, 343.7, 501.17

[56] References Cited

U.S. PATENT DOCUMENTS 3,917,704  11/1975  Kaiser et al. ................... 260/570.6

Primary Examiner—Robert V. Hines
Attorney, Agent, or Firm—Richard D. Foggio; William H. Edgerton

[57] ABSTRACT

α-Aminomethyl-4-hydroxy-3-methylsulfonyl benzyl alcohols having β-adrenergic antagonist activity are prepared generally from 4-benzyloxy-3-methylsulfonylacetophenone by, for example, bromination and treatment of the resulting α-bromo derivative with an N-benzyl secondary amine, followed by catalytic hydrogenation to remove protective benzyl groups and reduce the ketone moiety.

5 Claims, No Drawings

α-AMINOMETHYL-4-HYDROXY-3-METHYLSULFONYL BENZYL ALCOHOLS

This invention relates to novel substituted α-aminomethylbenzyl alcohols which have useful pharmacodynamic activity. More specifically the compounds of this invention are α-aminomethyl-4-hydroxy-3-methylsulfonyl benzyl alcohols and have utility as β-adrenergic antagonists.

The compounds of this invention are represented by the following general structural formula:

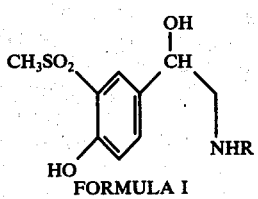

FORMULA I in which R represents lower alkyl, straight or branched chain, of from 1 to 6 carbon atoms, cycloalkyl or cycloalkylmethyl wherein the cycloalkyl moiety contains from 3 to 6 carbon atoms, $XC_6H_4CH_2CH(CH_3)$, $XC_6H_4CH_2C(CH_3)_2$ or $XC_6H_4CH_2CH_2CH(CH_3)$ and X is hydrogen, hydroxy, methoxy or methylenedioxy.

Advantageous compounds of formula I are those where R is isopropyl, t-butyl, cyclohexyl, 3-phenyl-2-propyl, 3-phenyl-2-methyl-2-propyl, 4-phenyl-2-butyl or 3-(p-hydroxyphenyl)-2-methyl-2-propyl.

The compounds of this invention may be used in the form of a pharmaceutically acceptable acid addition salt having the utility of the free base. Such salts, prepared by methods well known to the art, are formed with both inorganic or organic acids, for example: maleic, fumaric, benzoic, ascorbic, pamoic, succinic, bismethylenesalicylic, methanesulfonic, ethanedisulfonic, acetic, oxalic, propionic, tartaric, salicylic, citric, gluconic, lactic, malic, mandelic, cinnamic, citraconic, aspartic, stearic, palmitic, itaconic, glycolic, p-aminobenzoic, glutamic, benzenesulfonic, hydrochloric, hydrobromic, sulfuric, cyclohexylsulfamic, phosphoric and nitric acids.

The compounds of this invention are prepared by a sequence of reactions shown as follows:

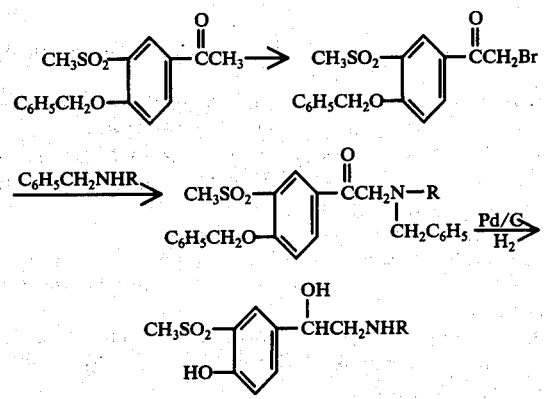

in which R is as defined in formula I. Thus, a methylsulfonyl acetophenone is treated with bromine or pyrrolidinone hydrotribomide to give the α-bromoacetophenone which is reacted with an N-benzylamine to give the corresponding α-benzylaminoacetophenone. This derivative is hydrogenated catalytically, preferably with palladium-on-carbon, to give the debenzylated benzyl alcohol product.

The methylsulfonyl acetophenone used as a starting material herein is prepared for example, from 2-methylsulfonyl phenol by acetylation, such as with acetic anhydride, to yield the acetoxy derivative which is treated with aluminum chloride in nitrobenzene to give 4-hydroxy-3-methylsulfonylacetophenone. The latter is reacted with benzyl chloride in the presence of potassium hydroxide or potassium carbonate to give the 4-benzyloxy-3-methylsulfonylacetophenone.

A preferred compound of this invention is α-(t-butylaminomethyl)-4-hydroxy-3-methylsulfonyl benzyl alcohol which causes attenuation of isoproterenol-induced increase of atrial contraction rate at a dose of $3.5 \times 10^{-6}$ M in an in vitro test using guinea pig right atria. Such action is indicative of β-adrenergic antagonist activity and therefore the compounds of this invention have use in the treatment of various cardiovascular disorders, for example, cardiac arrythmias, hypertension and angina pectoris.

The compounds of this invention may be administered orally or parenterally in conventional dosage unit forms such as tablets, capsules, injectables or the like, by incorporating the appropriate dose of a compound of formula I, with carriers according to accepted pharmaceutical practice. Preferably a compound or an acid addition salt thereof is administered orally to an animal subject in a tablet or capsule comprising an amount sufficient to produce β-adrenergic antagonist activity. Each dosage unit will contain the active medicament in an amount of about 20 mg. to about 300 mg. Advantageously, equal doses will be administered 2 to 4 times daily with the daily dosage regimen being about 40 mg. to about 1200 mg.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly the carrier or diluent can include any time delay material well known to the art, such as glyceryl monostearate or glyceryl distearate alone or with a wax.

A wide variety of pharmaceutical forms can be employed. Thus, if a solid carrier is used the preparation can be tableted, placed in a hard gelatin capsule in powder or pellet form, or in the form of a troche or lozenge. The amount of solid carrier will vary widely but preferably will be about 25 mg. to about 1 g. If a liquid carrier is used, the preparation will be in the form of a syrup, emulsion, soft gelatin capsule, sterile injectable liquid such as an ampul, or an aqueous or nonaqueous liquid suspension.

The foregoing is a general description of how to prepare the compounds of this invention. The following examples illustrate the preparation of specific compounds but should not be construed as a limitation of the invention.

EXAMPLE 1

A mixture of 38.4 g. (0.223 m.) of 2-methylsulfonyl phenol in 350 ml. of acetic anhydride is stirred at reflux for three hours and then evaporated to give the acetoxy derivative, m.p. 104°-106° C.

To a solution of 4.0 g. (0.020 m.) of the acetoxy compound in 25 ml. of nitrobenzene at room temperature is added 6.0 g. (0.045 m.) of aluminum chloride in portions. The reaction mixture is stirred at room temperature for about 1 hour and then at 50° C. for about 2 hours, followed by quenching in ice-water. The mixture is allowed to warm until above 5° C. and filtered to give 4-hydroxy-3-methylsulfonylacetophenone, m.p. 167.5°–168.5° C.

A mixture of 23.7 g. (0.118 m.) of the above-prepared acetophenone, 15 ml. (16.5 g., 0.130 m.) of benzyl chloride, 19.6 g. (0.142 m.) of potassium carbonate in 170 ml. of acetone and 120 ml. of water is refluxed overnight. The reaction mixture is poured into ice-water and filtered to obtain 4-benzyloxy-3-methylsulfonylacetophenone, m.p. 146.5°–147.5° C.

A mixture of 24.9 g. (0.0819 m.) of 4-benzyloxy-3-methylsulfonylacetophenone, 7.3 g. (0.086 m.) of 2-pyrrolidinone and 42.7 g. (0.086 m.) of pyrrolidinone hydrotribromide in tetrahydrofuran is refluxed two hours. The cooled reaction mixture is filtered and the filtrate is poured into water and stirred until crystallization occurs. The filtered solid is 4-benzyloxy-α-bromo-3-methylsulfonylacetophenone, m.p. 147.5°–148.5° C.

A mixture of 7.67 g. (0.0200 m.) of the above α-bromoacetophenone and 6.53 g. (0.0400 m.) of N-benzyl-t-butylamine in 100 ml. of acetonitrile is refluxed with stirring for four hours. The resulting solution is cooled in an ice-bath, allowed to stand overnight and filtered. The filtrate is diluted with ether, extracted with water, dried and evaporated to give a residue of α-(N-benzyl-t-butylamino)-4-benzyloxy-3-methylsulfonylacetophenone. The free base is acidified with ethereal hydrogen chloride, dissolved in 70% aqueous methanol and hydrogenated over 2.0 g. of 10% palladium-on-carbon at about 50 psi. The reaction mixture is filtered and evaporated in vacuo. The residue is dissolved in methanol, the solution cooled and the solid filtered to give α-t-butylaminomethyl-4-hydroxy-3-methylsulfonyl benzyl alcohol hydrochloride, m.p. 214.5° C. (dec.).

Similarly, employing N-benzylisopropylamine in the reaction with 4-benzyloxy-α-bromo-3-methylsulfonylacetophenone and proceeding as described above yields the corresponding product, α-isopropylaminomethyl-4-hydroxy-3-methylsulfonyl benzyl alcohol.

EXAMPLE 2

Following the procedures outlined in Example 1, 4-benzyloxy-α-bromo-3-methylsulfonylacetophenone is reacted with N-benzylcyclopentylamine to give α-(N-benzylcyclopentylamino)-4-benzyloxy-3-methylsulfonylacetophenone hydrochloride. Similar hydrogenation over palladium-on-carbon gives α-(cyclopentylaminomethyl)-4-hydroxy-3-methylsulfonyl benzyl alcohol.

Reacting 4-benzyloxy-α-bromo-3-methylsulfonylacetophenone with N-benzyl-4-methoxyphenylisopropylamine followed by hydrogenation furnishes the product α-[2-(4-methoxyphenyl)-1-methylethylaminomethyl-4-hydroxy-3-methylsulfonyl benzyl alcohol.

Similarly, employing N-benzylcyclopropylmethylamine or N-benzylmethylamine in the above reaction followed by hydrogenation there is obtained α-(cyclopropylmethylaminomethyl)-4-hydroxy-3-methylsulfonyl benzyl alcohol or 4-hydroxy-α-(methylaminomethyl)-3-methylsulfonyl benzyl alcohol, respectively.

EXAMPLE 3

Following the procedures of Example 1, 4-benzyloxy-α-bromo-3-methylsulfonylacetophenone is reacted with N-benzylphenylisopropylamine to give 4-benzyloxy-α-(N-benzylphenylisopropylamino)-3-methylsulfonylacetophenone which is hydrogenated to yield 4-hydroxy-3-methylsulfonyl-α-(2-phenyl-1-methylethylaminomethyl) benzyl alcohol.

Reacting 4-benzyloxy-α-bromo-3-methylsulfonylacetophenone with N-benzyl-4-benzyloxyphenylisopropylamine followed by hydrogenation gives 4-hydroxy-α-[2-(4-hydroxyphenyl)-1-methylethylaminomethyl]-3-methylsulfonyl benzyl alcohol.

EXAMPLE 4

As described in Example 1, 4-benzyloxy-α-bromo-3-methylsulfonylacetophenone is refluxed with N-benzyl-3,4-methylenedioxyphenylisopropylamine to give 4-benzyloxy-α-(N-benzyl-3,4-methylenedioxyphenylisopropylamino)-3-methylsulfonylacetophenone. Catalytic hydrogenation yields 4-hydroxy-α-[2-(3,4-methylenedioxyphenyl)-1-methylethylaminomethyl]-3-methylsulfonyl benzyl alcohol.

Similarly, reaction of the bromoacetophenone with N-benzyl-2-(4-benzyloxyphenyl)-1,1-dimethylethylamine to give 4-benzyloxy-α-[N-benzyl-2-(4-benzyloxyphenyl)-1,1-dimethylethylamino]-3-methylsulfonylacetophenone followed by the above described catalytic hydrogenation yields the product 4-hydroxy-α-[2-(4-hydroxyphenyl)-1,1-dimethylethylaminomethyl]-3-methylsulfonyl benzyl alcohol.

EXAMPLE 5

| Ingredients | Mg./Tablet |
|---|---|
| α-(t-Butylaminomethyl)-4-hydroxy-3-methylsulfonyl benzyl alcohol* | 50 |
| Lactose | 100 |
| Starch | 7 |
| Magnesium stearate | 0.7 |

*Added as the hydrochloride salt

A granulation of the above ingredients is compressed with punches having 9/32 inch diameter. What is claimed is:

1. A chemical compound of the formula:

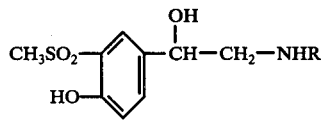

or a pharmaceutically acceptable acid addition salt of said compound, wherein:
R is straight or branched chain lower alkyl of from 1 to 6 carbon atoms, cycloalkyl or cycloalkylmethyl, the cycloalkyl moiety having from 3 to 6 carbon atoms, $XC_6H_4CH_2CH(CH_3)$, $XC_6H_4CH_2C(CH_3)_2$ or $XC_6H_4CH_2CH_2 CH(CH_3)$; and
X is hydrogen, hydroxy or methoxy.

2. A chemical compound according to claim 1 which is α-(t-butylaminomethyl)-4-hydroxy-3-methylsulfonyl benzyl alcohol.

3. A chemical compound according to claim 1 which is α-(cyclopentylaminomethyl)-4-hydroxy-3-methylsulfonyl benzyl alcohol.

4. A chemical compound according to claim 1 which is 4-hydroxy-α-(methylaminomethyl)-3-methylsulfonyl benzyl alcohol.

5. A chemical compound according to claim 1 which is 4-hydroxy-α-[2-(4-hydroxyphenyl)-1,1-dimethylethylaminoethyl]-3-methylsulfonyl benzyl alcohol.

* * * * *